United States Patent
Moutou et al.

(10) Patent No.: US 9,315,455 B2
(45) Date of Patent: Apr. 19, 2016

(54) PROCESS FOR ISOMERIZING FUSED BICYCLIC STRUCTURES AND PREPARATION OF VITAMIN D ANALOGS COMPRISING THE SAME

(75) Inventors: Jean-Luc Moutou, Cagnes sur Mer (FR); Florent Mouton, Saint-Laurent du Var (FR); Gilles Pellegrino, Menton (FR); Jean Lafay, Nice (FR)

(73) Assignee: HYBRIGENICS SA, Paris (FR)

( * ) Notice: Subject to any disclaimer, the term of this patent is extended or adjusted under 35 U.S.C. 154(b) by 114 days.

(21) Appl. No.: 13/012,084

(22) Filed: Jan. 24, 2011

(65) Prior Publication Data

US 2011/0184198 A1    Jul. 28, 2011

(30) Foreign Application Priority Data

Jan. 26, 2010   (EP) ..................................... 10305088

(51) Int. Cl.
*C07C 401/00* (2006.01)
*C07C 45/67* (2006.01)

(52) U.S. Cl.
CPC ............... *C07C 401/00* (2013.01); *C07C 45/67* (2013.01); *C07B 2200/07* (2013.01); *C07C 2102/24* (2013.01)

(58) Field of Classification Search
USPC .................. 552/624, 653; 568/341
See application file for complete search history.

(56) References Cited

U.S. PATENT DOCUMENTS

| | | |
|---|---|---|
| 6,017,907 A | 1/2000 | Bouillon et al. |
| 6,548,715 B1 | 4/2003 | Bouillon et al. |
| 7,414,158 B2 | 8/2008 | Aouad et al. |
| 8,481,514 B2 | 7/2013 | Delansorne et al. |
| 2008/0021246 A1 | 1/2008 | Aouad et al. |
| 2011/0184198 A1 | 7/2011 | Moutou et al. |

FOREIGN PATENT DOCUMENTS

WO    WO 2006/042383    4/2006

OTHER PUBLICATIONS

Deuben et al. (The stereochemistry of Hydride Reduction, Jun. 5, 1956, p. 2579).*
Zhu and Okamura (Chemical Reviews, 1995, vol. 95, No. 6, pp. 1877-1952).*
Zhao et al. (AN 144:70007, CASREACT, abstract of European Journal of organic chemistry (2005), (20), 4414-4427).*
Wu et al. (AN 136:85987 CASREACT, abstract of European Journal of organic chemistry (2001), (20),3779-3788).*
Wu et al. (European Journal of organic chemistry (2001), (20), 3779-3788).*
Extended European Search Report for EP 10305088.6.
Wu, et al., "A Practical Synthesis of 14-*epi*-19-*nor*-1α,25-Dihydroxyvitamin $D_3$ Analogues and Their A-ring Epimers", 2001, pp. 3779-3788, Eur. J. Org. Chem. (Full Version).

* cited by examiner

*Primary Examiner* — Sabiha N Qazi
(74) *Attorney, Agent, or Firm* — B. Aaron Schulman, Esq.; Stites & Harbison, PLLC.

(57) ABSTRACT

The present invention concerns a process of isomerizing trans fused bicyclic derivatives into cis fused bicyclic derivatives and the preparation of vitamin D or analogs thereof comprising said isomerization step.

Figure:

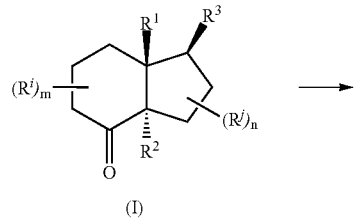

(I)

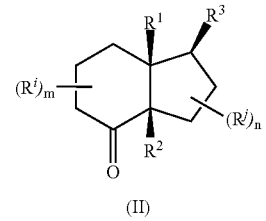

(II)

8 Claims, No Drawings

PROCESS FOR ISOMERIZING FUSED BICYCLIC STRUCTURES AND PREPARATION OF VITAMIN D ANALOGS COMPRISING THE SAME

The present invention is concerned with a new process for isomerizing fused bicyclic structures and a process for preparing vitamin D analogs comprising the same.

Vitamin D is a pro-hormone, meaning that it has no hormone activity itself but is converted into the active hormone through a regulated synthesis mechanism. Several forms of vitamin D have been discovered, including D1-D5. Chemically, the various forms of vitamin D are secosteroids, in which one of the bonds in the steroid rings is broken. The various forms of vitamin D differ from the side chains. Vitamin D receptors belong to the nuclear receptor super family of steroid/thyroid hormone receptors and are expressed by cells in most organs, including the brain, heart, skin, gonads, prostate and breast. Vitamin D receptor activation in the intestine, bone, kidney and parathyroid gland cells leads to the maintenance of calcium and phosphorus levels in the blood and to the maintenance of bone content (Holick et al., *American Journal of Clinical Nutrition* 81(6) 1678S-88S). Vitamin D receptor is also known to be involved in cell proliferation and differentiation. Vitamin D also affects the immune system as vitamin D receptors are expressed in several white blood cells including monocytes and activated T and B cells.

To increase the therapeutic potential of the natural vitamin D, analogs have been synthesized with increased potency for specific action and several vitamin D analogs have been developed such as seocalcitol, inecalcitol, elocalcitol, exacalcitol.

Vitamin D analogs are now recognized for their potent role in cell proliferation and cell differentiation making them promising drugs candidates for the treatment of cancer patients.

Inecalcitol 1 is the international non-proprietary name for (7E)-19-nor-9,10-seco-14β-cholesta-5,7-dien-23-yne-1α, 3β,25-triol ($C_{26}H_{40}O_3$) (WHO Drug Information, Vol 17, No. 2, 2003) of formula:

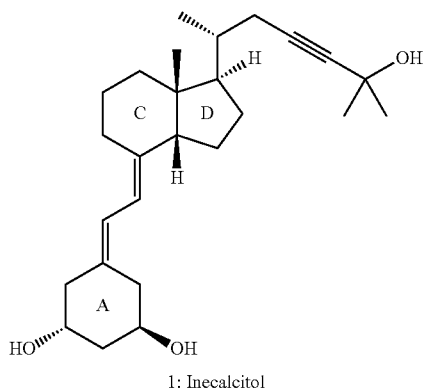

1: Inecalcitol

It is a synthetic derivative of calcitriol, the natural active metabolite of vitamin D3. Inecalcitol, however, is ten times more potent and one hundred times less toxic than calcitriol. This profile has positioned inecalcitol as an effective drug candidate, initially for the treatment of hormone resistant prostate cancer. Unlike other vitamin D analogs, Inecalcitol structure is characterized by a cis C/D ring junction. Processes of vitamin D analogs comprising a cis C/D ring are in particular disclosed in U.S. Pat. No. 6,017,907. It includes the coupling of the cis C/D moiety derivative with a corresponding A ring derivative, which, in the case of inecalcitol, can be illustrated by the following scheme:

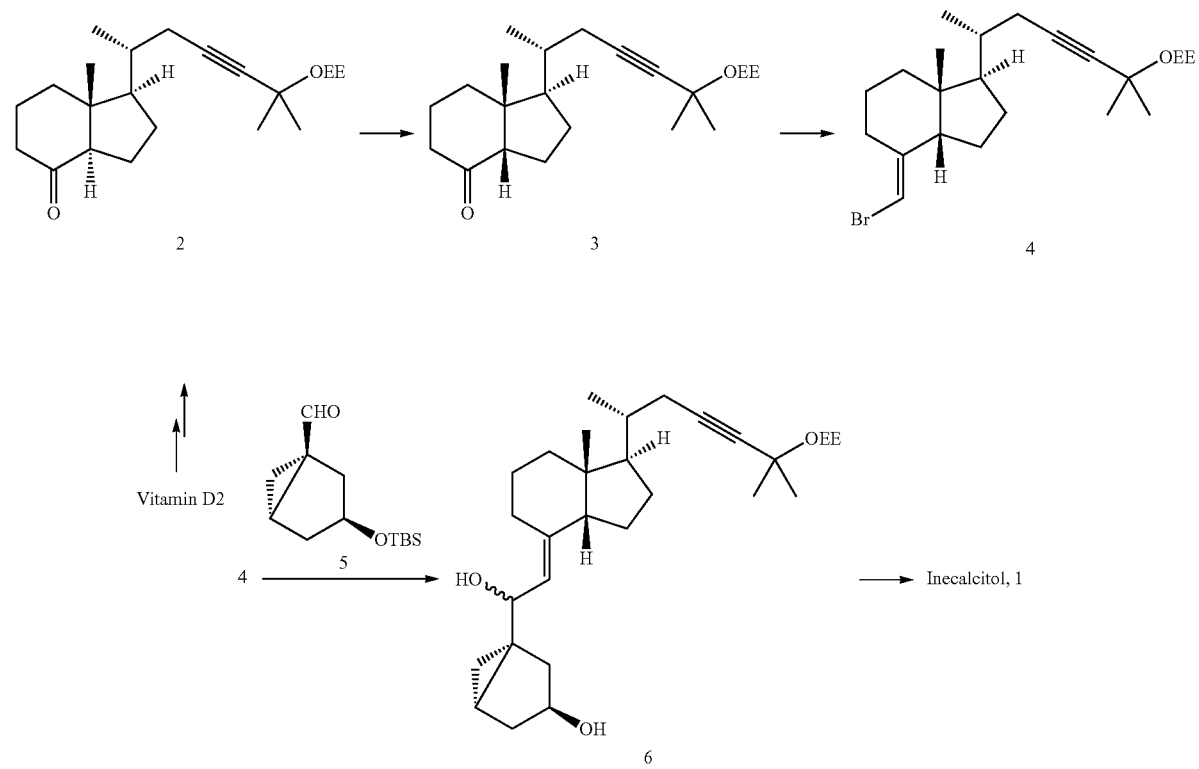

The cis C/D ring junction is obtained from epimerization of the corresponding trans C/D ring. U.S. Pat. No. 6,017,907 teaches that epimerization attempted on diverse protected ketones can be carried out in the presence of NaOMe, MeOH, at room temperature, during 24 hours, and always leads to the expected epimerization with a circa 3/1 ratio in favor of the cis isomer and 60-70% yield, according to the scheme:

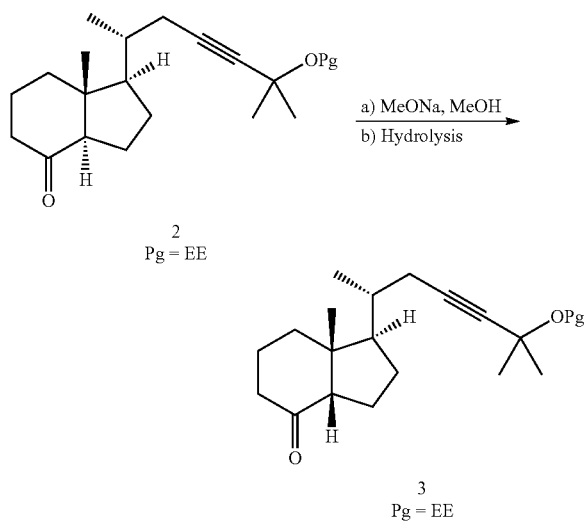

However, this reaction, performed in the gram scale, afforded the desired pure cis isomer only after careful separation by HPLC, which appeared to be problematic in the scaled-up synthesis and industrial processes. For instance, in the 100 g scale, the inventors obtained a cis/trans ratio of 78/22, which required three successive chromatographic purifications in order to afford pure cis compound (98/02 cis/trans) with only 49% yield. They also found that in the kg scale, iterative chromatographic separations lead to unsatisfying diastereomeric ratio and purity of the cis C/D ketone: several purifications were actually needed in order to raise the desired purity (95/05) including recycling of 50/50 mixtures.

It is therefore highly desirable to provide a new process for isomerizing a trans bicyclic fused structure into the corresponding cis bicyclic fused structure with higher selectivity. The present inventors have now surprisingly discovered new experimental conditions allowing very satisfying yields and higher ratios of isomerisation, convenient working conditions, compliant with industrial scales. This represents an important simplification of the process of preparation of Inecalcitol and other putative vitamin D analogs with cis C/D ring junctions.

According to a first object, the present invention thus concerns a process of preparation of a cis fused bicyclic derivative from a corresponding trans fused bicyclic derivative, said process comprising the step of reacting said trans fused bicyclic derivative with an hydride base Suitable bases may be chosen from those of formula M-H, where M is an atom of the IA group, such as KH or NaH, more preferably NaH.

The base is preferably in excess. The concentration of the base is comprised between 1 and 2 equivalents of that of the trans starting product, preferably around 1.5.

Said reaction may be carried out at a temperature comprised between room temperature and the boiling temperature of the reaction mixture. Preferably, the reaction may be carried out at the reflux temperature.

Said reaction may be carried out during a time sufficient for achieving a satisfying yield. The duration can be comprised between a few minutes and one day, more preferably between 1 and 12 hours.

The reaction is generally conducted in a suitable organic solvent such as THF, alkylated THF including Me-THF, toluene, more preferably THF.

According to a preferred aspect, said fused bicyclic derivative is chosen from fused bicyclic systems comprising a cycloalkanone fused with a cycloalkyl. Said cycloalkanone and cycloalkyl may be chosen from optionally substituted cyclohexanone, cyclopentanone, cyclohexane, cyclopentane.

Said fused bicyclic derivative is preferentially chosen from those systems comprising an optionally substituted cyclohexanone, more particularly an optionally substituted cyclohexanone fused with an optionally substituted cyclopentane (so called "C/D rings").

<<Optionally substituted>> herein refers to optional, one or more substituents of said cycloalkanone and said cycloalkyl, being independently chosen from H, halogen atom, $C_1$-$C_6$ alkyl, $C_2$-$C_6$ alkenyl, OR, NRR', CN, NO$_2$, perhalogeno($C_1$-$C_6$)alkyl, COR, COOR, CONRR', alkylaryl, alkenylaryl, where R, R', identical or different, are chosen from H, alkyl, aryl.

According to another embodiment, said trans and cis fused bicyclic structures are respectively of formula (I) and (II):

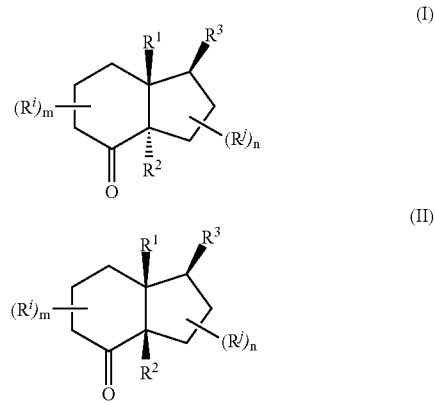

in which:
R$^1$ represents H or a $C_1$-$C_6$ alkyl group;
R$^2$ represents H or D;
where D represents a deuterium atom;
R$^3$ represents a $C_1$-$C_{20}$ alkyl, optionally comprising one or more double or triple bonds, and/or optionally interrupted by one or more heteroatom(s) selected from O, N, S, Si; preferably, R$^3$ is a linear or branched $C_1$-$C_{20}$ alkyl, $C_2$-$C_{20}$ alkenyl, $C_2$-$C_{20}$ alkynyl, said alkyl, alkenyl or alkynyl being optionally substituted by one or more group(s) chosen from OH or a protective group of the OH function. Said protective group is preferably chosen from acid labiles groups such as ketals: ethoxyethyle (EE), or fluoride labiles group such as trialkyls silyls groups: trimethylsilyl (TMS), triethylsilyl (TES), tert-Butyldimethylsilyl (TBS), trisisopropylsilyl (TIPS), tert-butyldiphenylsylil (TBDPS);
m is an integer chosen from 0, 1, 2, 3;
n is an integer chosen from 0, 1 or 2;
when present, each R$^i$ and R$^j$, identical or different, respectively represent 1 to n or 1 to m groups, identical or different from each other, and are independently chosen from halogen atom, $C_1$-$C_6$ alkyl, $C_2$-$C_6$ alkenyl, OR, NRR', CN, $NO_2$, perhalogeno($C_1$-$C_6$)alkyl, COR, COOR, CONRR', alkylaryl, alkenylaryl, where R, R', identical or different, are chosen from H, alkyl, aryl.

More preferably:
m=n=0;
$R^1$=methyl;
$R^2$=H; and/or
$R_3$ is of formula:

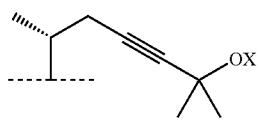

where X is H or X is a protective group of the OH function, and the broken bond ⟶ is the bond to the cyclopentyl core.

Generally, the process of the invention also comprises a hydrolysis step, conducted after the above isomerisation step. Said hydrolysis is conducted by routine hydrolysis procedure, such as contacting the reaction mixture with water.

The process of the invention may also comprise the purification of the obtained cis fused bicyclic derivative, by standard procedures. As HPLC is no longer required, said purification is preferably not HPLC, according to a particular embodiment of the process of the invention.

The purification may be advantageously conducted by chromatography, such as column chromatography. Any type of column may be used, including usual glass columns, although pre-packed columns, such as Flashsmart columns, may be preferred. The eluting solvent is advantageously a mixture of an alcane, an ester or a mixture thereof, such as a mixture of heptane and ethylacetate. A preferred mixture is heptane/ethylacetate in a ratio from 70:30 to 95:5, preferably around 90:10.

The eluting solvent may additionally comprise a base such as TEA.

According to a further object, the present invention also concerns the process of preparation of a steroid or secosteroid derivative having a cis C/D ring function, said process comprising the process of preparation of a cis fused bicyclic derivative according to the invention.

Said secosteroid is preferably an analog of vitamin D, more preferably inecalcitol or a derivative thereof, of formula (III).

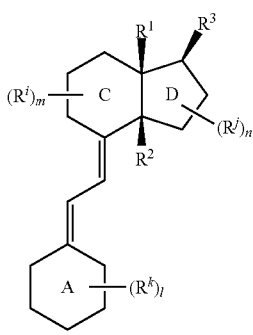

(III)

where $R^1$, $R^2$, $R^3$, $R^i$, $R^j$, m, n are defined as in formula (I) and l is an integer chosen from 0, 1, 2, 3 or 4 and each $R^k$, identical or different from each other, is independently chosen from halogen atom, $C_1$-$C_6$ alkyl, $C_2$-$C_6$ alkenyl, OR, NRR', CN, $NO_2$, perhalogeno($C_1$-$C_6$)alkyl, COR, COOR, CONRR', alkylaryl, alkenylaryl, where R, R', identical or different, are chosen from H, alkyl, aryl.

The process of preparation of said analog of vitamin D further comprises:
  conducting a Wittig reaction;
  coupling the obtained compound with a corresponding cyclohexane derivative or a precursor thereof; and, optionally,
  hydrolyzing the obtained compound.

The Wittig reaction leading to a vinyl halide derivative is generally carried out by means of a triphenylphosphine derivative, such as an ylide, such as $Ph_3PCH(Hal)_2$ where Hal represents a halogen atom such as Br. This reaction can be conducted under usual Wittig conditions, in particular at a temperature between −80° and −50° C. This step may be followed by one or more purification step(s) such as chromatography. The ylide may be prepared by reacting a corresponding alkyl halide with triphenylphosphine ($PPh_3$). Vandewalle et al (*Tetrahedron Lett*, 37, 7637-7640, 1996), demonstrated that no epimerization take place at this stage.

Following the Wittig reaction, the following compound is obtained, according to a preferred embodiment:

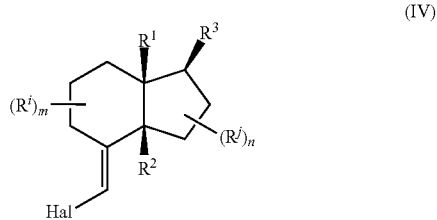

(IV)

The coupling step is preferably conducted by means of a cyclohexane derivative or bicyclic precursor thereof, such as a compound of formula (V):

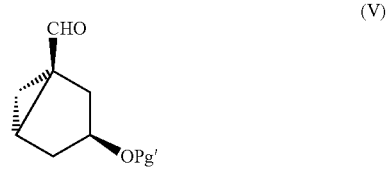

(V)

where Pg' is a protecting group of the OH function. Preparation of compounds of formula (V) is described in U.S. Pat. No. 6,191,292.

The coupling proceeds via metal-halogen exchange generally conducted in the presence of a strong lithiated base such as n-BuLi, s-BuLi or t-BuLi, more preferably t-BuLi.

The coupling reaction leads to a compound of formula (VI):

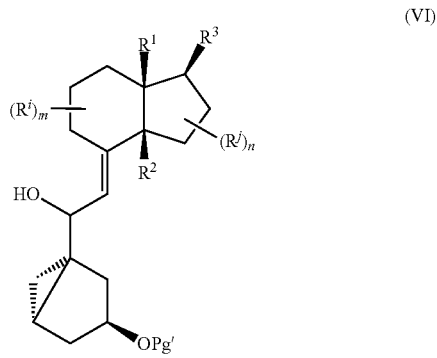

(VI)

Optional hydrolysis of compound of formula (VI) leads via rearrangement to a compound of formula (VII):

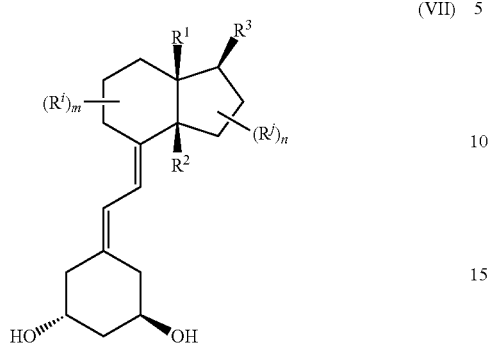

Generally, the hydrolysis may be conducted by an acid-catalysed solvolysis in dioxane/water, in the presence of an acid such as TsOH. With these conditions, removal of the ethoxyethyl protecting group takes place affording the crude Inecalcitol, purified via crystallization.

The steps starting from compound of formula (II) to vitamin D or an analog thereof are known in the art, in particular from U.S. Pat. No. 6,017,907, and can be completed by the skilled person by applying or adapting such known methods.

The starting products of the processes of the invention are commercially available or may be prepared by the skilled person by applying and adapting known methods.

As used herein, "steroid or secosteroid derivative having a cis C/D ring junction" refers to derivatives comprising the following scaffold:

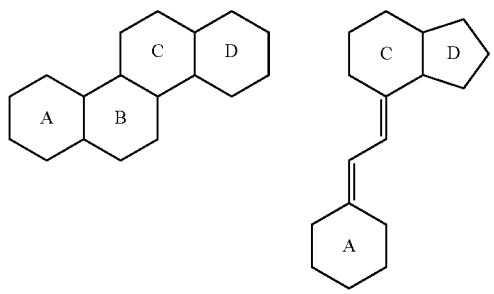

wherein the C and D cycles are arranged to form a cis ring junction.

As used therein, the expression "analog of vitamin D" refers to vitamin D derivatives comprising a cis C/D ring system, such as inecalcitol.

The terms "precursor thereof" used herein refer to a compound which differs from the indicated or desired compound by the presence and/or absence of one or more function(s). Such function(s) may be introduced, transformed and/or omitted by common functionalization reactions, known from the skilled person.

The term "corresponding" as used therein refers to starting compounds, reagent, intermediate and/or obtained compounds involved in a reaction and, that, hence, have the same substitution, excepted from the moiety affected by said reaction.

The following examples are given for illustrating non-limiting purpose.

EXAMPLE 1

(1R,3aS,7aR)-1-((2S)-5-(1-ethoxyethoxy)-5-methyl-hex-3-yn-2-yl)-7a-methylhexahydro-1H-inden-4(2H)-one (3)

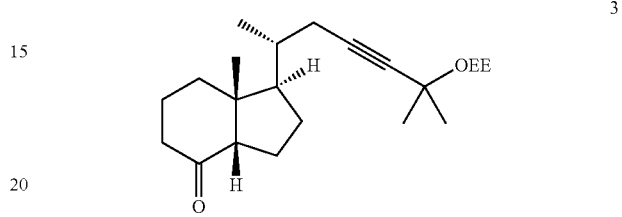

The trans ketone 2 (1 g) was stirred under reflux in THF in the presence of an excess (1.5 eq) of NaH for 4 hours. A cis/trans ratio of 96/4 was obtained (determined by HPLC). Then the reaction mixture was poured at room temperature on water at 10° C. The cis/trans ratio was not affected by this hydrolysis. Gel chromatography was carried out on silica (15 weight equivalent), eluting with a mixture of heptane/AcOEt+TEA (90/10). 680 mg (68%) of the desired cis product were obtained with a purity >99%. The collected analytical data were in accordance with the structure of 3.

EXAMPLE 2

Example 1 was reiterated with scaled-up quantities, as follows 2.1. A solution of trans ketone 2 (299 g, 0.851 moles) in Tetrahydrofuran (1.5 L) was slowly added to sodium hydride 60% (52 g, 2.16 moles) in suspension in Tetrahydrofuran (1.5 l). When the addition was completed the mixture was stirred for 0.5 hours at room temperature and boiled under reflux for 4 hours. The solution was then cooled and water (1.5 L) was added. The mixture was stirred and extracted with n-Heptane. The organic layer was washed with water and concentrated. Crude product was purified by flash chromatography on silica gel to give pure cis ketone 3 (215 g, yield 75%, cis/trans ratio 97/3). The collected analytical data were in accordance with the structure of 3.

2.2. A solution of trans ketone 2 (2.640 kg, 7.57 moles) in Tetrahydrofuran (13 L) was slowly added to sodium hydride 60% (464 g, 19.33 moles) in suspension in Tetrahydrofuran (14 L). When the addition was completed, the mixture was stirred for 0.5 hours at room temperature and boiled under reflux for 4 hours. The solution was then cooled and water (14 L) was added. The mixture was stirred and extracted with n-Heptane. The organic layer was washed with water and concentrated. Crude product was purified by flash chromatography on silica gel to give cis ketone 3 (1.850 kg, yield 69%, cis/trans ratio 97/3). The collected analytical data were in accordance with the structure of 3.

EXAMPLE 3

Preparation of Inecalcitol 3.1. Formation of Vinyl Bromide 4

A solution of Potassium bis(Trimethylsilyl)amide (484 g, 2.42 moles) in Tetrahydrofuran (2.2 L) was slowly added at −30° C. b a solution of (Bromomethyl)Triphenylphosphonium Bromide (1.124 kg, 2.57 moles) in Tetrahydrofuran (2.2 L). When the addition was completed, the mixture was kept for 1.5 hours at −30° C. and then warmed to 0° C. A solution of cis ketone 3 (340 g, 0.975 mole) in Tetrahydrofuran (0.5 L) was then added at 0° C. and the mixture was stirred for 2.5 h. Water was then slowly added, while maintaining the temperature lower than 20° C. The mixture was extracted with ethylacetate. The organic layer was washed with brine, dried and concentrated. The crude residue was purified by flash chromatography on silica gel to give pure vinylbromide 4 (200 g, yield 48%).

3.2. Condensation with Aldehyde 5

A solution of tert-butyllithium (1.7 M in Pentane, 1.25 L) was added dropwise at −70° C. to a solution of 4 (431 g, 1.01 mole) in Tetrahydrofuran (3.4 L). When the addition was completed, the mixture was stirred for 1.5 h at −70° C. and a solution of aldehyde 5 (253 g, 1.05 mole) in Tetrahydrofuran (0.5 L) was added dropwise to the mixture. The solution was then kept 1 hour at −70° C. and quenched by addition of a saturated Ammonium Chloride solution. The solution was extracted with ethylacetate and organic layers were then washed with brine, dried and concentrated. The crude residue was purified by flash chromatography on silica gel to give pure compounds 6 (308 g, yield 51%).

3.3. Synthesis of Inealcitol 1

A solution of p-Toluenesulfonic Acid (57 g, 0.299 moles) in Dioxane/Water (120 mL, 7/3) was added to a solution of compound 6 (305 g, 0.505 moles) in Dioxane/Water (4 L). The mixture was stirred at 60° C. for 4 hours, and then cooled to room temperature. Ethyl acetate was added, and the solution was washed with a saturated aqueous solution of Sodium Hydrogencarbonate, and brine. The organic layer was separated, dried and concentrated. The crude residue was purified by flash chromatography on silica gel and crystallized from Diisopropylether/Ethanol to give pure Inecalcitol 1 (145 g, yield 71%).

COMPARATIVE EXAMPLE 1

According to U.S. Pat. No. 6,017,907

The isomerisation of 370 mg of the trans compound used in example 1 is carried out in the presence of a MeONa/MeOH mixture, at room temperature for 12 hours. The mixture is evaporated, under reduced pressure, the residue is purified on a silicagel column (ethyl acetate/hexane 2/8) and the pure cis ketone is obtained upon separation by HPLC (ethyl acetate: hexane 2:8) with a yield of 65%.

COMPARATIVE EXAMPLE 2

Comparative Example 1 was reiterated on scale-up quantities:

A solution of sodium methoxide (30 wt % in methanol, 73 ml) was added dropwise to a solution of the trans ketone 2 (538 g, 1.55 moles) in methanol (5.4 L) at 10° C. When the addition was completed the mixture was stirred for 3 hours at 50° C. The solution was then cooled to room temperature and filtered on silica gel (1 Kg). The filtrate was concentrated to afford 522 g of crude cis ketone 3 (cis/trans ratio of 80/20). The crude residue was separated in two portions and each portion was purified by flash chromatography on silica gel (2×2 Kg, eluent n-Heptane/Ethyl acetate (9/1)). The purification was monitored by HPLC.

The fractions showing a cis/trans ratio ≥95/5 were combined and concentrated to give pure cis ketone 3 (144 g, yield 27%, cis/trans ratio 97/3). The fractions showing a cis/trans ratio between 85/5 and 95/5 were combined, concentrated and submitted to a second flash chromatography on silica gel (2 Kg, eluent n-Heptane/Ethylacetate (9/1)). Fractions showing a cis/trans ratio ≥95/5 were combined and concentrated to give additional pure cis ketone 3 (117 g, yield 22%, cis/trans ratio 98/2). Finally, the pure materials were combined to afford 261 g of pure cis ketone 3 (yield 49%, cis/trans ratio 97/3).

Note: The fractions showing a cis/trans ratio ≤85/15 from the 3 columns were combined and concentrated to give 217 g of a crude mixture containing mainly cis ketone 3 and trans ketone 2 (cis/trans ratio 52/48). This fraction could be again isomerised using the conditions described above to afford a crude mixture of 3 (cis/trans ratio 80/20). The tedious purification technique using several flash chromatographies could be repeated in order to slightly increase the total yield of the synthesis.

COMPARATIVE EXAMPLE 3

The isomerisation of the trans compound used in example 1 is carried out in the following various conditions. The obtained ratios are reported in the table below:

| Solvent | Base | Temperature | Duration | Yields (cis:trans) |
|---|---|---|---|---|
| MeOH/H$_2$O | NaOH | 50° C. | 24 h | 76:24 |
| MeOH | MeONa | Reflux | 24 h | 80:20 |
| THF | MeONa 5% | Reflux | 24 h | 84:16 |
| Me—THF/H$_2$O | NaOH 5% | Reflux | 24 h | 84:16 |
| tBuOH | tBuOK 5% | Reflux | 24 h | 75:25 |

It is apparent that none of the various bases tested leads to a cis:trans ratio higher than 84/16, wherein the use of a hydride base leads to a cis:trans ratio >96/4.

The invention claimed is:
1. A process of preparation of inecalcitol of formula:

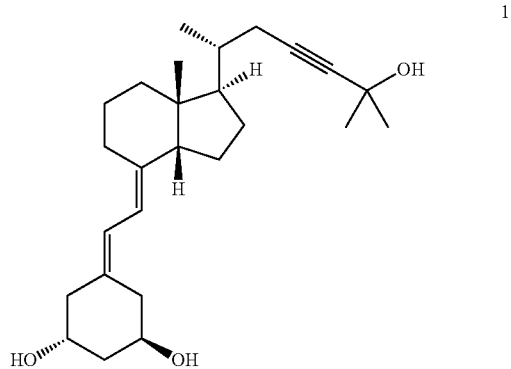 [SMILES: C[C@H](CC#CC(C)(C)O)[C@H]1CC[C@@H]2/C(=C/C=C3C[C@@H](O)C[C@H](O)C3)CCC[C@@]21C]

said process comprising the process of preparation of a cis fused bicyclic compound of formula (II) from a corresponding trans fused bicyclic compound of formula (I):

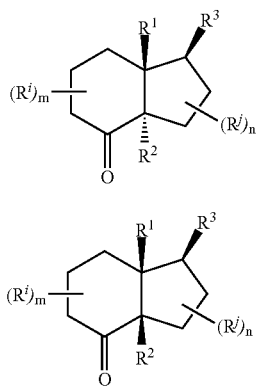

said process comprising the step of reacting said trans fused bicyclic compound with an hydride base which is NaH or KH, wherein in formulae (I) and (II):
m=n=0,
R$^1$=methyl,
R$^2$=H; and
R$_3$ is of formula:

where X is H or X is a protective group of the OH function, and the broken bond is the bond of the cyclopentyl core; and said process of preparation of the compound of formula (II) being followed by the transformation of said compound of formula (II) into inecalcitol in one or more steps.

2. The process according to claim 1 further comprising the steps of:
conducting a Wittig reaction leading to a vinyl halogenide compound;
coupling the obtained compound with a corresponding cyclohexane compound or a precursor thereof; and optionally
hydrolyzing the obtained compound.

3. The process according to claim 1 further comprising the steps of:
conducting a Wittig reaction leading to a vinyl halogenide compound;
coupling the obtained compound with a corresponding cyclohexane compound or with a compound of formula (V):

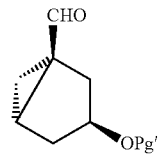

where Pg' is a protecting group of the OH function; and optionally
hydrolyzing the obtained compound.

4. The process according to claim 1, wherein said step is conducted in a solvent chosen from THF or an alkylated THF.

5. The process according to claim 1 further comprising an hydrolysis step, conducted after the above isomerization step.

6. The process according to claim 1 further comprising the purification of the obtained cis compound of formula (II).

7. The process according to claim 6, wherein said purification is carried out by column chromatography.

8. The process according to claim 7, wherein the eluting solvent is a mixture of heptane and ethylacetate.

* * * * *